US005680215A

United States Patent [19]
Huber et al.

[11] Patent Number: 5,680,215
[45] Date of Patent: Oct. 21, 1997

[54] VISION INSPECTION SYSTEM AND METHOD

[75] Inventors: Edward D. Huber, Sunnyvale; Rick A. Williams, Orinda, both of Calif.

[73] Assignee: Lockheed Missiles & Space Company, Inc., Sunnyvale, Calif.

[21] Appl. No.: 395,847

[22] Filed: Feb. 27, 1995

[51] Int. Cl.$^6$ .................................................. G01B 11/30
[52] U.S. Cl. ............................ 356/371; 356/73; 356/237
[58] Field of Search .................................. 356/371, 237, 356/445, 446, 376, 237 G

[56] References Cited

U.S. PATENT DOCUMENTS

| | | | |
|---|---|---|---|
| 3,762,818 | 10/1973 | Johnson et al. | 356/376 |
| 4,641,972 | 2/1987 | Halioua et al. | 356/376 |
| 4,794,550 | 12/1988 | Greivenkamp, Jr. | 356/357 |
| 4,825,263 | 4/1989 | Desjardins et al. | 356/376 |
| 5,058,178 | 10/1991 | Ray | 356/237 |
| 5,189,481 | 2/1993 | Jann et al. | 356/237 |
| 5,247,344 | 9/1993 | Doan | 356/237 |
| 5,307,152 | 4/1994 | Boehnlein et al. | 356/376 |
| 5,311,286 | 5/1994 | Pike | 356/371 |
| 5,471,308 | 11/1995 | Zeien | 356/376 |
| 5,497,234 | 3/1996 | Haga | 356/371 |
| 5,557,410 | 9/1996 | Huber et al. | 356/376 |
| 5,561,526 | 10/1996 | Huber et al. | 356/376 |

FOREIGN PATENT DOCUMENTS

| | | | |
|---|---|---|---|
| 0213509 | 8/1989 | Japan | 356/371 |
| 4109106 | 4/1992 | Japan | 356/371 |

OTHER PUBLICATIONS

David R. Burton and Michael J. Lalor, 'Multichannel Fourier fringe analysis as an aid to automatic phase unwrapping', Applied Optics, May 10, 1994, vol. 33, No. 14, U.S.A.

Katherine Creath, 'Wyko Systems for Optical Metrology', 1987, SPIE Proceeding, vol. 816 Interferometry Metrology, U.S.A.

Chris L. Koliopoulos and Mark Jensen, 'Real–Time Video Rate Phase Processor', 1993, pp. 264–268, SPIE vol. 2003, Interferometry VI, U.S.A.

Daniel Malacara, Optical Shop Testing, 1992, pp. 668–681, "Moiré and Fringe Projection Techniques", John Wiley & Sons, Inc., U.S.A.

Carolyn R. Mercer and Glenn Beheim, 'Fiber–Optic Projected–Fringe Digital Interferometry', Nov. 4–7, 1990, pp. 1–8, NASA Technical Memorandum 103252, U.S.A.

B.F. Oreb, K.G. Larkin, P. Fairman and M. Ghaffari, 'Moire based Optical Surface Profiler for the Minting Industry', 1992, pp. 48–57, SPIE Proceeding vol. 1776, U.S.A.

James C. Wyant, 'Interferometric Optical Metrology: Basic Principles and New Systems', May 1982, pp. 65–71, Laser Focus, U.S.A.

Yiping Xu and Chiayu Ai, 'Simple and effective phase unwrapping technique', 1993, pp. 254–263, SPIE vol. 2003, Interferometry VI, U.S.A.

Primary Examiner—Hoa Q. Pham
Attorney, Agent, or Firm—Fenwick & West LLP

[57] ABSTRACT

An optical vision inspection system (4) and method for multiplexed illuminating, viewing, analyzing and recording a range of characteristically different kinds of defects, depressions, and ridges in a selected material surface (7) with first and second alternating optical subsystems (20, 21) illuminating and sensing successive frames of the same material surface patch. To detect the different kinds of surface features including abrupt as well as gradual surface variations, correspondingly different kinds of lighting are applied in time-multiplexed fashion to the common surface area patches under observation.

22 Claims, 6 Drawing Sheets

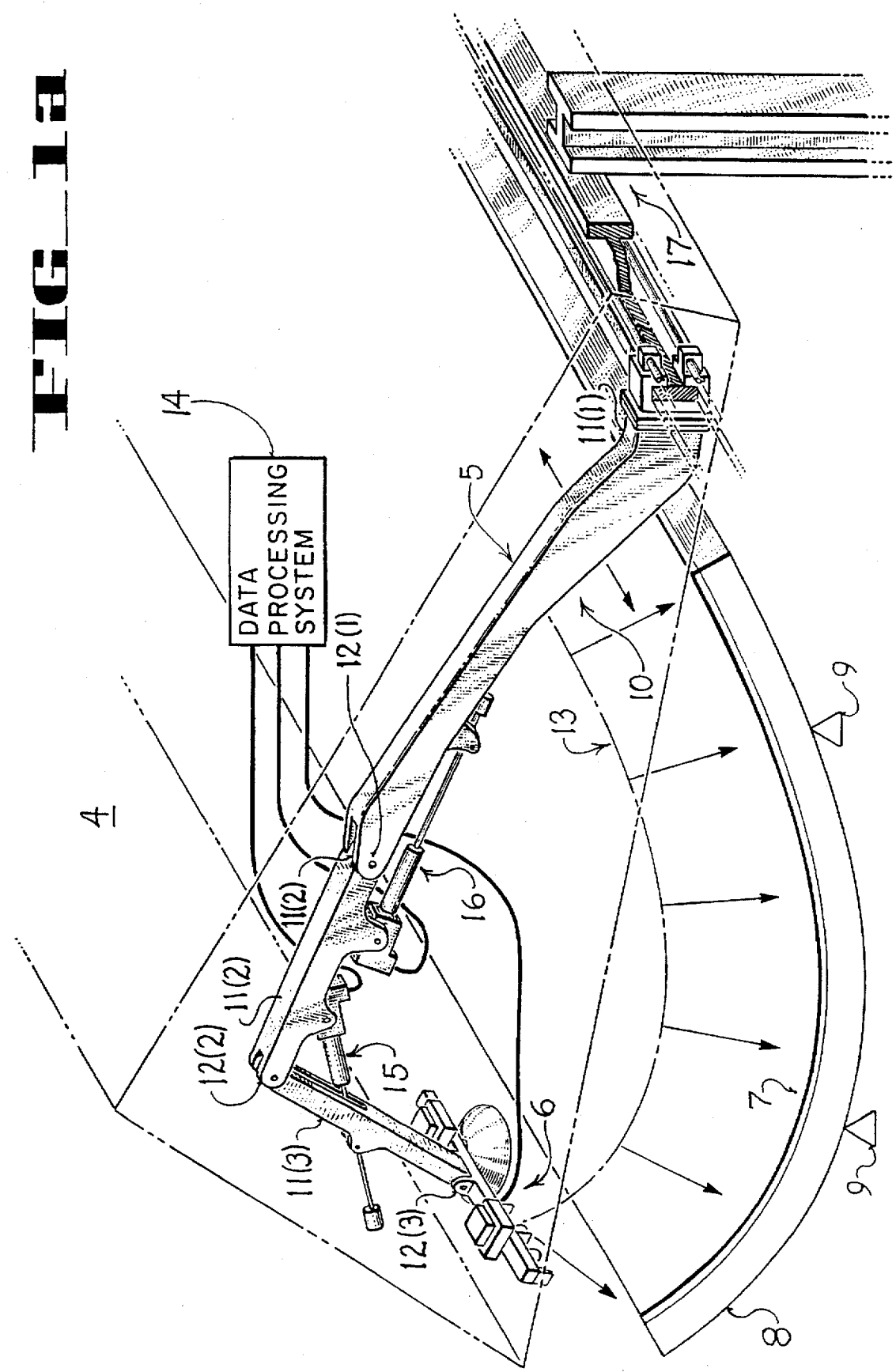

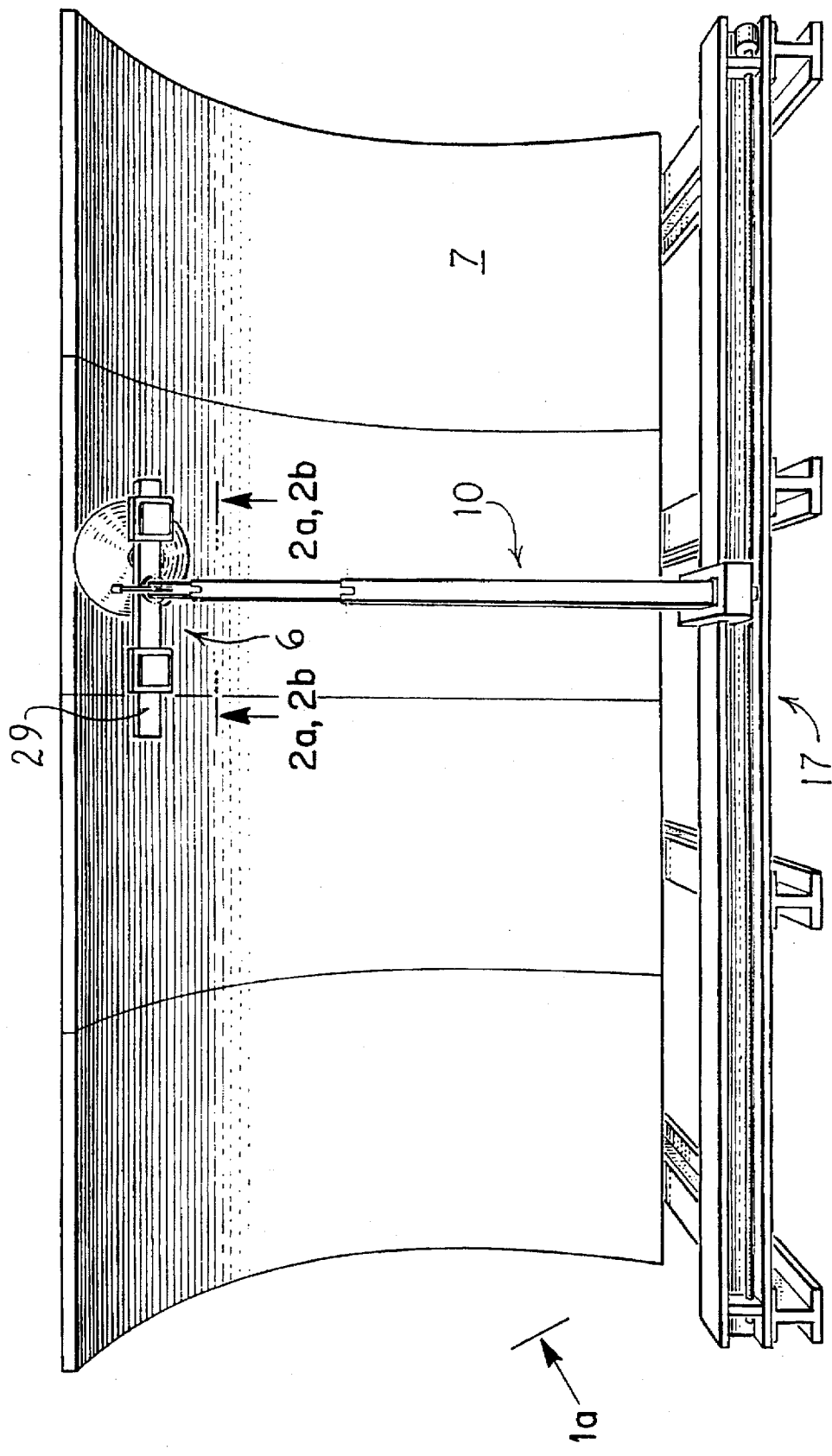

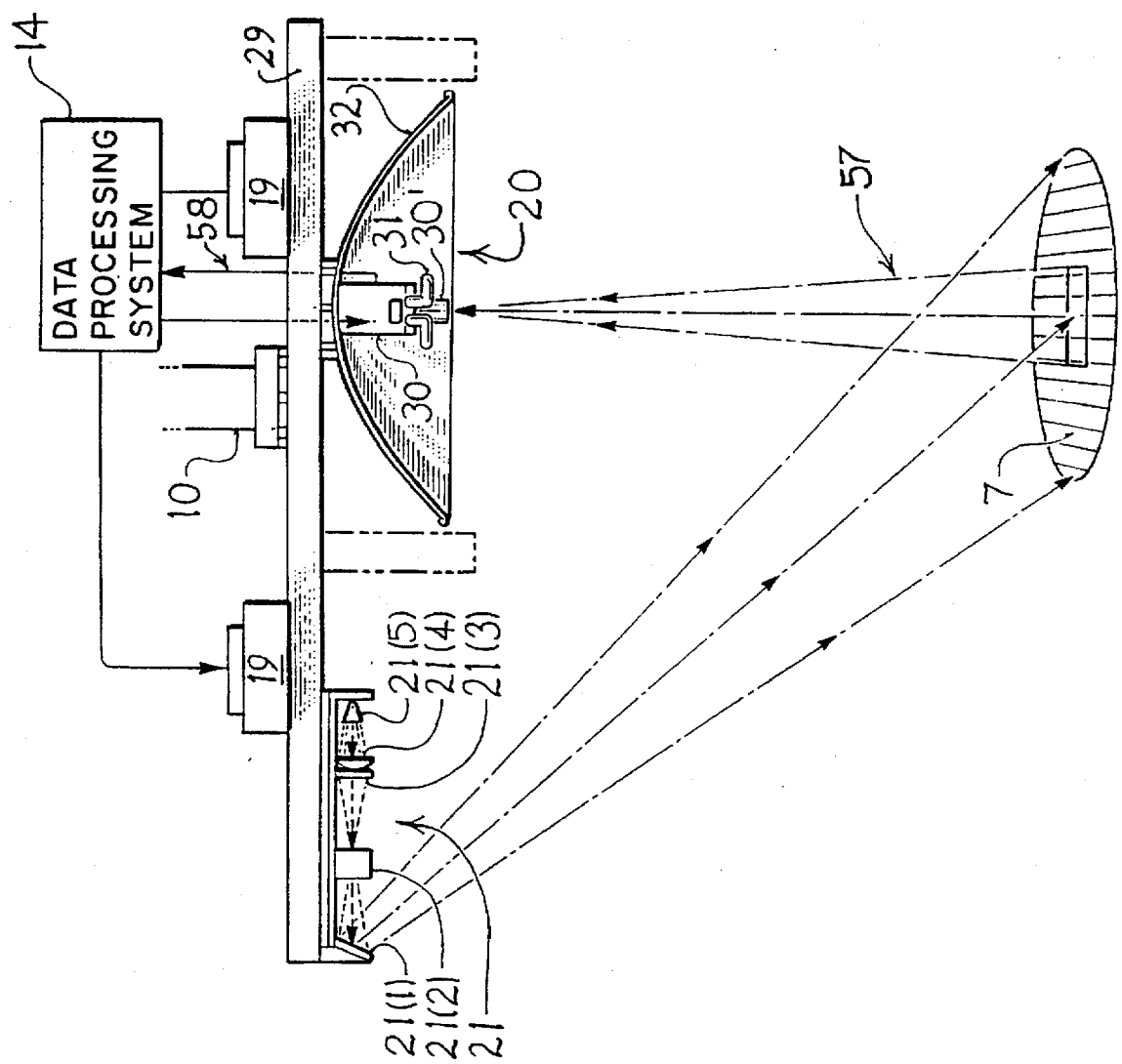
FIG_2a

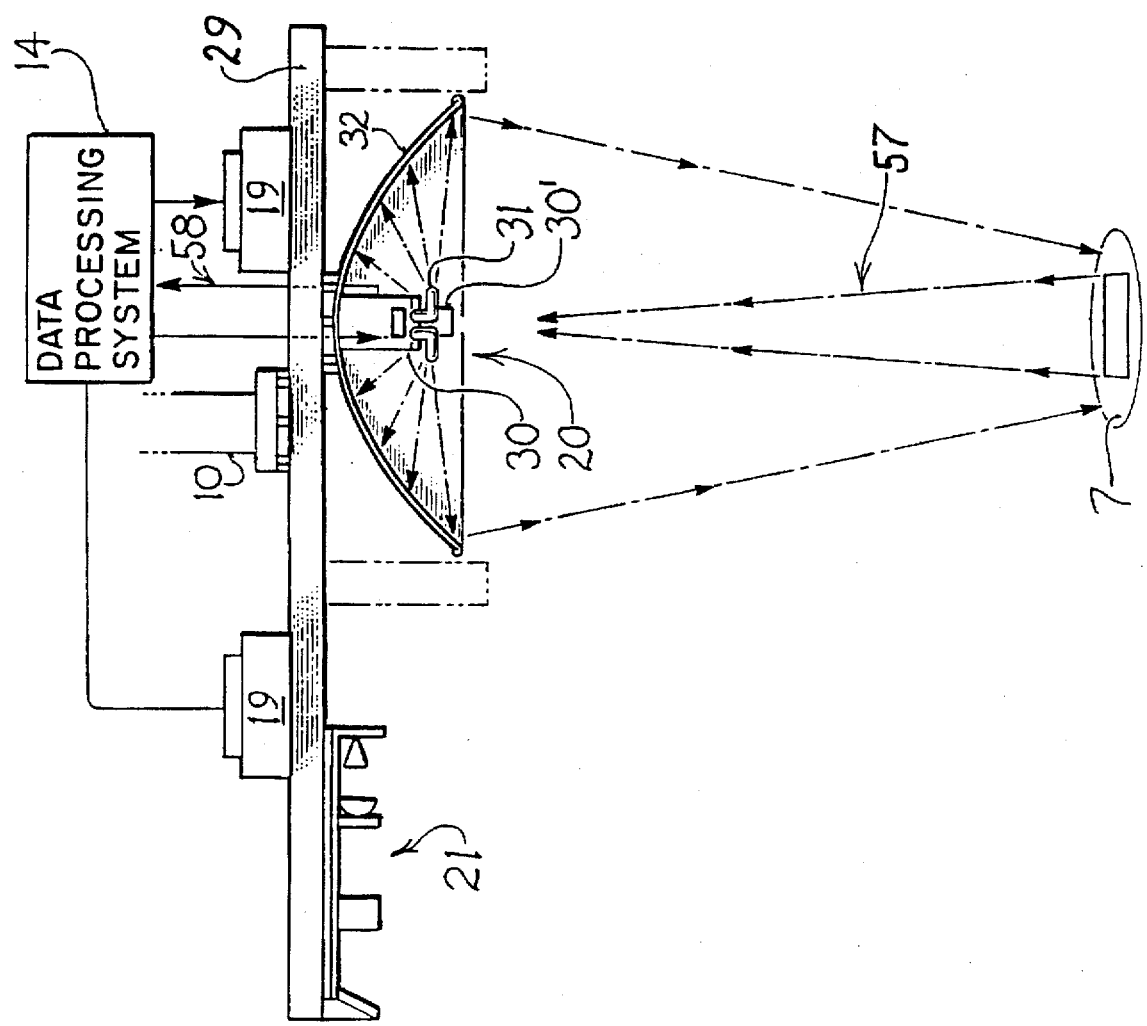
FIG_2b

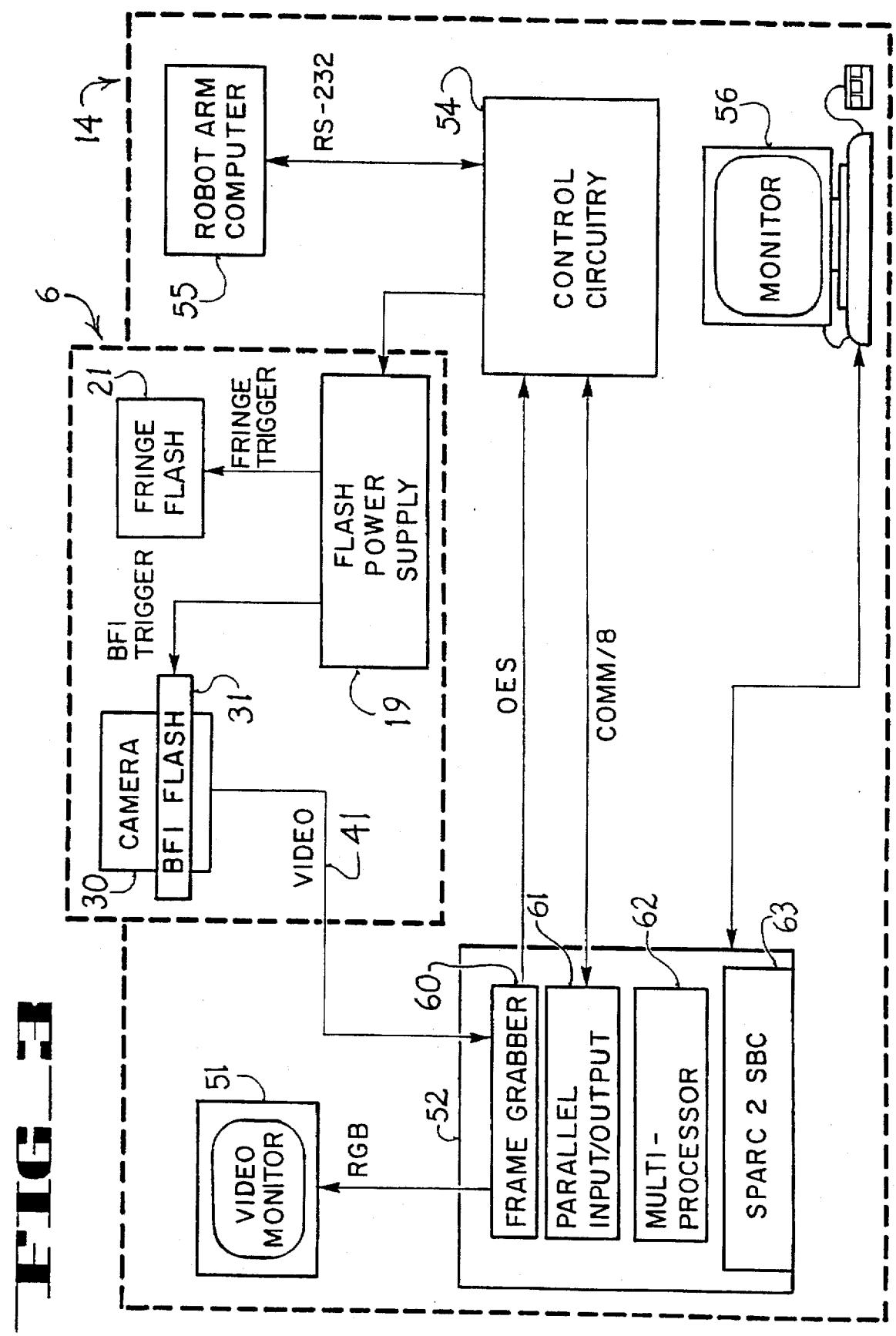

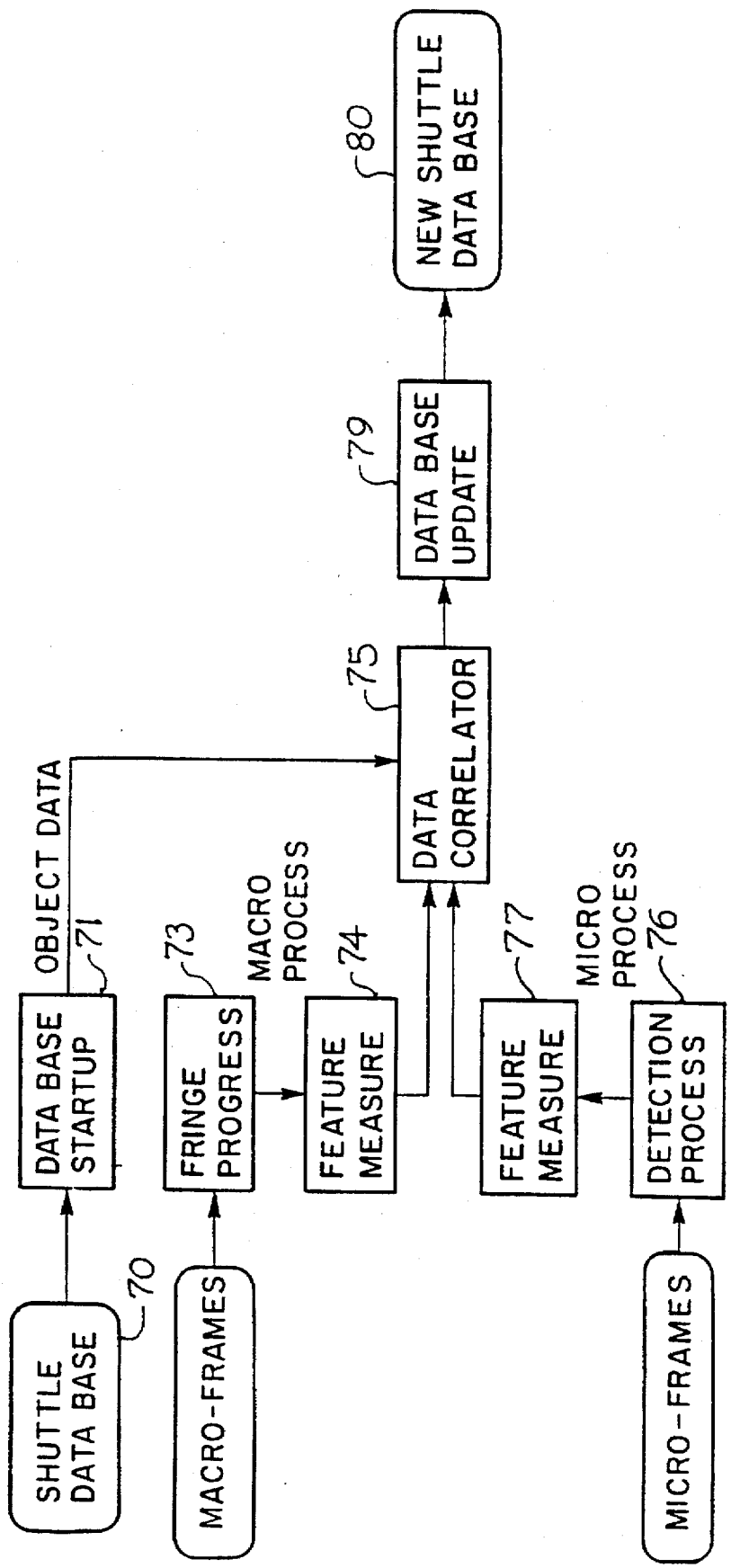

VISION INSPECTION SYSTEM AND METHOD

STATEMENT OF GOVERNMENTAL INTEREST

This invention was made in part using funds provided under NASA contract NAS 10-10900. As such, the U.S. government has rights in this invention.

CROSS-REFERENCE TO RELATED APPLICATIONS

This application is related to U.S. patent application Ser. No. 08/249,841 filed on May 26, 1994 to inventors Edward D. Huber, Rick A. Williams, Dean M. Shough, Osuk Y. Kwon, and Rebecca L. Welling, and entitled "CONTOUR MEASUREMENT SYSTEM." This patent application is assigned to the same assignee as herein and is incorporated herein by reference in its entirety. This patent application was abandoned in favor of FWC application Ser. No. 08/569,524 filed Dec. 8, 1995 now U.S. Pat. No. 5,612,786.

TECHNICAL FIELD

This invention relates generally to vision inspection systems and methods, and more particularly to vision systems and methods for inspection of material surfaces having a range of defect kinds.

BACKGROUND OF THE INVENTION

Rapid inspection of large surfaces having different kinds of damage distributed irregularly to varying degrees of frequency is frequently problematic, particularly when it is desired to compare a current surface under inspection with a prior recorded surface data base. At present, damage inspections of particular kinds of material surfaces are on occasion done visually by a human inspector, operating perhaps with the aid of a magnifying glass and flashlight. This manual approach is unfortunately slow, labor intensive and tedious. Further, manually generated inspection data is not readily accessible for review and analysis, because it is typically not already entered into a computer data base and requires further manual data entry and keyboarding subject to risk of human error. An example of the kinds of surfaces which may require rapid and reliable inspection, measurement, and comparison with prior inspection results are the thermal radiators or cargo-bay doors of a space shuttle. The radiators need to be inspected before and after every flight into space. The radiators are composite structures having a honeycombed core covered by an aluminum sheet overlaid by Permacel P-223 including Kapton and silicone adhesive and layers of Inconel, silver, and Teflon.

Currently the radiators are visually inspected, a task requiring up to three people working several shifts to complete the visual inspection. Among different kinds of shuttle damage targeted for identification and characterization are microdamage features including punctures, scratches, and gouges over 0.005 inch in depth; and macrodamage features including dents over 0.008 inch in depth and over 0.25 inches in diameter, and delaminations over 0.008 inches in depth and over 0.25 square inches in area. It is desired that these damage features be localized within approximately plus or minus 0.1 inch. The particular kinds of surfaces inspected include thermal reflective tape, aluminum skin, and coolant flow lines.

SUMMARY OF THE INVENTION

According to the present invention, a vision inspection system (4) and method provides for multiplexed illumination and data handling of multiple kinds of surface characteristics including abrupt and gradual surface variations and differences between measured characteristics of different kinds and prior measurements. The present invention makes provision to illuminate and identify both microfeatures as well as macrofeatures in selected material surfaces, permitting enhanced camera discrimination of the various kinds of features. According to the present invention, damage artifacts which are orders of magnitude smaller in lateral dimension extent than the others which may be much broader laterally without a comparable lateral contrast gradient, can be detected and measured. Such macrofeatures may be very gradual depth depressions or elevations, as when the damage is a delamination causing a formerly undeviated surface level to rise at a gradual rate with a lateral traversal. According to the present invention, assessment to a high degree of reliability, of damage to embossed, specular, and highly reflective surfaces which have very few damage sites, i.e., typically from zero to five (but on occasion up to hundreds of damage sites) over a surface having hundreds of non-damaged features in a very large surface area covering more than 100 square meters, is made possible.

More particularly, the present invention provides a vision inspection system (4) that can accurately measure the size and shape of cavities, ridges and depressions in material surfaces (7) of two basic kinds: micro damage, such as pin hole punctures, scratches, and cuts; and macro damage, such as shallow dents and tape material delaminations, for example. The vision inspection system (4) according to the present invention automatically finds and identifies both large and small damage sites on selected material surfaces (7). The vision inspection system (4) according to the present invention is robotically mounted for automated scanning operation. Further, the optical system (4) according to the present invention assesses, with high reliability, information with respect to damage to embossed, specular and highly reflective surfaces (7) having very few damage sites. Typically zero to five, but on occasion hundreds, would be present among hundreds of non damaged features over a very large surface area covering more than 100 square meters. The inspection process is performed at a high rate to cover a large inspection surface area quickly.

The vision inspection system (4) according to the present invention further characterizes damage sites on a selected material surface (7) with first and second optical subsystems (20, 21). The first optical subsystem (20) highlights and finds small damage sites having cuts, scratches or micrometeor damage using a uniform broad source illuminator that emphasizes abrupt damage sites to be detected by a video camera system. The second optical subsystem (21) is designed to highlight and measure larger, gradual damage areas such as dents and bubbles or delaminations of radiator tape on a space shuttle surface, for example. This optical subsystem uses a white light projector to illuminate the radiator surface with fringe lines for surface contour measurement that is sensitive to surface deformations. The combination of these optical subsystems covers the expected range of damage with a high level of reliability. Video image data from optical subsystems is acquired and processed using a data processing system (14) conducting several stages of image processing and analysis enabling each damage site to be identified and fully characterized. The inspection data is stored in a new or revised database as a feature list for each damage site, and the large volume of video data processed is either discarded or archived.

During data acquisition in accordance with one embodiment of the present invention, first and second successive image frames are captured for the same illuminated region or patch of predetermined size, and inspection processing begins the interpretation of each of the two images separately. In particular, a micro-damage analysis according to the present invention processes diffuse illumination data taken from microdamage locations to assess damage such as punctures or scratches, after a series of image processing and analysis steps to filter background clutter and characterize each damage site in terms of specific features such as location, size, shape, for example. The macro-damage detection procedure processes acquired fringe data to evaluate larger damage areas such as shallow dents or tape delaminations for generating a 3-D depth profile map which is filtered to remove background noise. Then, each damage site is characterized in terms of specific features. The accumulated damage or object data is stored in a data base available for follow-up testing, evaluation and reporting.

BRIEF DESCRIPTION OF THE DRAWINGS

FIG. 1a is a side schematic diagram of the vision inspection system according to the present invention, including robotic and optical systems for multiplexed illumination and inspection of a material surface which may have defects of several characteristically different kinds;

FIG. 1b is a top schematic diagram of the vision inspection system according to the present invention, including robotic and optical systems for multiplexed illumination and inspection of the same material surface;

FIG. 2a shows a schematic diagram of the optical system according to the present invention, including two optical subsystems for multiplexed illumination of a material surface which may have defects of several characteristically different kinds, with indications of the operation of illumination by a second subsystem using fringe lines and the detection of the fringe lines by a video camera with respect to a predetermined patch of a selected material surface;

FIG. 2b shows a side schematic diagram of the optical system according to the present invention, including two optical subsystems for multiplexed illumination of a material surface which may have defects of several characteristically different kinds, with indications of the operation of diffuse illumination by a first optical subsystem and the detection of the illuminated surface by a video camera with respect to a predetermined patch having abrupt contour defects or variations;

FIG. 3 shows a block diagram of the vision inspection system according to the present invention, including an embodiment of the present invention having an optical system and a data processing system; and FIG. 4 is a flow chart of operation of a vision inspection system according to the present invention.

DETAILED DESCRIPTION OF THE PREFERRED EMBODIMENTS

FIG. 1a is a side schematic diagram of a vision inspection system 4 according to the present invention, including a portion of robot system 5, an optical system 6, and a data processing system 14, for multiplexed illumination and inspection of a selected material surface 7 which may have defects of several characteristically different kinds. In particular, material surface 7 of FIG. 1a may be metallic, ceramic, or comprised of selected composite materials. FIG. 1b is a top view of the elements shown in side view in FIG. 1a. In the case of material surface 7 being a radiator door of a shuttle space vehicle, material surface 7 to be inspected may be a tape overlayer including laminations which are joined to a selected metallic undersurface 8. Undersurface 8 may in turn be held in place during inspection by selected supports 9. Robot system 5 according to the present invention includes an arm 10 including one or more limbs 11 respectively connected with joints 12, more particularly referred to as joints 12(1)–12(3). Limbs 11 include first through third limbs 11(1)–11(3). Limbs 11 are positionable relatively with respect to each other at joints 12 under control of data processing system 14 providing suitable electric control signals to drive C, for example, hydraulic apparatus 15 and 16. Hydraulic apparatus 15 is connected to respective extensions of limbs 11(1) and 11(2), and hydraulic apparatus 16 is connected to respective extensions of limbs 11(2) and 11(3). Limb 11(1) is mounted on a laterally positionable frame 17 which adjusts arm 10 and optical system 6 axially along the contour of material surface 7 continuously or intermittently as arm 10 and optical system 6 inspect sections of material surface 7 along path 13. Thus, robot system 5 is used for positioning optical system 6 for vision inspection of selected material surface 7 along successive paths 13. Optical system 6 according to the present invention accomplishes multiplexed illumination and inspection of a material surface 7 which may have defects of several characteristically different kinds, including, microdamage including for example, abrupt defects including punctures and scratches; and macrodamage, including, for example, gradual defects including shallow dents or tape delaminations.

One embodiment of optical system 6 according to the present invention is shown in FIG. 2a including first and second optical subsystems 20 and 21 and a video camera 30. FIG. 2b shows these elements with an emphasis on the operation of first optical subsystem, while FIG. 2a emphasizes the operation of the second optical subsystem 21. Video camera 30 receives images from selected portions of surface 7 while illuminated by optical system 6. Video camera 30 is preferably electronic and desirably has sufficient resolution capabilities to detect imperfections, irregularities, and defects on or of material surface 7 which are targeted for detection. Electronic video camera 30 may look directly down or obliquely onto material surface 7 from a distance of about two feet above, for example. Visual scanning is accomplished by viewing approximate 5 inch by 5 inch patches during scanning in a continuous motion about 24 inches above the target surface under inspection, according to one embodiment of the present invention. Information is collected in predetermined data frames using strobed illuminators that "freeze" the motion of the scanner as data is taken every 4 inches along a predetermined sweep path. As an alternative to a video camera other kinds of image detectors can be employed.

As indicated in FIGS. 1a and 1b, vision inspection system 6 is mounted on arm 10 of robot system 5. An embodiment of the present invention including vision inspection system 6 is shown in FIGS. 2a and 2b including a flash system 19, first and second optical subsystems 20 and 21, support structure 29, and a video camera 30, which are subject to control of data processing system 14 for directing the operation and positioning of robot system 5 as well as the timing of illumination bursts from first and second optical systems 20 and 21. Flash system 19 produces trigger signals which activate a selected one or both of first and second optical subsystems 20 and 21. First and second optical subsystems 20 and 21 accomplish multiplexed illumination of material surface 7. More particularly, robot system 10 controls the positioning of optical system 6 over selected portions and paths for viewing and illuminating material surface 7. Robot system 10 may for example conduct a raster illumination and detection scan of material surface 7. Optical subsystems 20 and 21 according to the present invention include respective first and second illumination systems, which are employed for illuminating material surface 7. Alignment of optical systems 20 and 21 ensures that first and second illumination systems 20 and 21 are positioned with respect to common portions of material surface 7 for visual inspection.

In lieu of separate optical subsystems 20 and 21, a single illumination system can be used, so long as the system is capable of producing time-separate illumination beams for multiplex operation, to provide suitable lighting to enable detection of different kinds of surface defects, irregularities, or damage. Optical subsystems 20 and 21 are multiplexed, by strobing for example, to provide illumination to predetermined patches along a specified path on material surface 7 by lighting first from one and then from the other of optical subsystems 20 and 21. Predetermined blank periods of non-illumination can be provided between pulses or strobes of one form of illumination and then the other. Further, more than two modes of illumination may be provided by use of additional separate illumination systems or optical subsystems, or by use of a single system which is constructed to produce selectably multiplexed lighting suitable for detection and measurement of different kinds of defects or surface variations including abrupt and gradual surface variations.

FIG. 2a particularly shows a side schematic diagram of vision inspection system 6 according to the present invention, including first and second optical subsystems 20 and 21 and support structure 29 mounted at or near its center to joint 12(3). Vision inspection system 6 accomplishes multiplexed illumination of material surface 7 with first and second optical subsystems 20 and 21. According to the preferred embodiment of the present invention indicated in FIGS. 2b and 2a, first and second optical subsystems 20 and 21 are both strobed illumination systems working with single video camera 30. First optical subsystem 20, according to an embodiment of the present invention, is a diffuse illumination system, which comprises a ring flash lamp 31 and an elliptical reflector 32. Ring flash lamp 31 is preferably mounted around video camera 30 and elliptical reflector 32 is located behind video camera 30 and ring flash lamp 31. Both ring flash lamp 31 and video camera 30 are located at or near one focus of elliptical reflector 32. The other focal point of elliptical reflector 32 is located approximately twice the distance to material surface 7 from the one focus of elliptical reflector 32, so that return light from material surface 7 uniformly fills the lens of video camera 30 over its entire viewing area.

FIG. 2b shows a side schematic diagram of first optical subsystem 20 according to an embodiment of the present invention, for accomplishing diffuse illumination of a selected patch of material surface 7 which may have defects with abrupt contour variations. In particular, first optical subsystem 20 comprises ring flash lamp 31 mounted along a central axis of the concave surface of elliptical reflector 32. Axially oriented video camera 30 including viewing lens 30' is mounted along the axis of elliptical reflector 32 and within the annulus of ring flash lamp 31. Ring flash lamp 31 is preferably mounted around the viewing lens 30' of video camera 30, and elliptical reflector 32 is located behind video camera 30 and ring flash lamp 31. Both ring flash lamp 31 and video camera 30 are located at one focus of elliptical reflector 32. The other focal point of elliptical reflector 32 is located approximately twice the distance to material surface 7, so that return light from material surface 7 uniformly fills the lens of video camera 30 over its entire viewing area.

Second optical subsystem 21 shown in FIGS. 2a and 2b is a slide projection type system (referred to as a fringe projector according to one embodiment of the present invention) which images a grating onto material surface 7. Details of the fringe projection approach are provided in related U.S. patent application Ser. No. 08/249,841 filed on May 26, 1994 to inventors Edward D. Huber, Rick A. Williams, Dean M. Shough, Osuk Y. Kwon, and Rebecca L. Welling, and entitled "CONTOUR MEASUREMENT SYSTEM." This patent application is assigned to the same assignee as herein and is incorporated herein by reference in its entirety. This patent application was abandoned in favor of FWC application Ser. No. 08/569,524 filed Dec. 8, 1995 now U.S. Pat No. 5,612,786. Second optical subsystem 21 can be mounted onto a selected end of boom 29 as shown in FIGS. 2a and 2b. Second optical subsystem 21 according to one embodiment of the present invention is two feet in length, so that the angle between the fringe projector and video camera 30 is preferably about forty-five degrees. Video camera 30 receives image information from material surface 7 along image beam path 57 which is converted into a video signal provided along video line 58 to data processing system 14, which may be a general purpose computer or a processor of much simpler design and construction. The video information provided to data processing system 14 includes the results of illumination provided by both first and second optical subsystems 20 and 21. According to one embodiment of the present invention, the fringe projector of second optical subsystem 21 is any projector capable of illuminating material surface 7 with a set of fringe lines. The fringe projector may use a white light or a monochromatic light source. It may provide continuous, flash, or strobe illumination. The boresight of the light emanating from second optical system 21 may be perpendicular to material surface 7 or it may form an other than 90° angle therewith. The fringe lines falling on material surface 7 are made to have a sinusoidally varying intensity as seen by camera 30; this variation is in the x (horizontal) direction in the preferred embodiment. The fringe lines represent lines of maximum intensity. They are vertically disposed in this embodiment. These lines are 360° apart in phase. A selected fringe line establishes a reference for phase and position calculations during calibration and measurement operational modes. Camera 30 has a field of view encompassing all or part of a selected portion of material surface 7. Camera 30 may be any electronic camera, such as a CCD, CID, or Vidicon camera or film. The boresight of camera 30 may be perpendicular to material surface 7, or may form an other than 90° angle therewith. The image plane of camera 30 is divided into a set of pixels, e.g., 640 horizontal×480 vertical pixels. Camera 30 may or may not employ frame integration. The image data recorded by camera 30 are fed into data processing system 14. Control circuitry 54 in FIG. 3 is coupled between computer 52 and vision inspection system 6. The purpose of control circuitry 54 is to synchronize camera 30 with vision inspection system 6 and its optical subsystems 20 and 21, in part when optical subsystem 21 is flashing or strobing, within a projector to produce fringe lines patterns on material surface 7 in a spatial phase shifting embodiment. Fringe lines projected onto material surface 7 that are not completely straight and exhibit bumps in the horizontal dimension indicate the presence of a contour on material surface 7, i.e., a change in its depth (z) dimension. According to one embodiment of the present invention, a three-bucket algorithm with three frames, or a four-bucket algorithm is used, wherein the frames are, relatively speaking, at 0° phase, 90° phase, 180° phase, and 270° phase for reasons indicated below. The four-bucket algorithm is less prone to errors than the three-bucket algorithm, but takes more processing time. Another alternative method is the Carré method. In the Carré method, the phase shifts between frames can be other than 90°. These are just three examples of algorithms borrowed from phase-shifting interferometry. Any phase-shifting algorithm may be used in the present invention. Following the calculation of the phase map and the unwrapping of the phases, the computed phases are then converted into calculated three-dimensional coordinates by applying the system calibration parameters to each pixel data point, using the system geometry equations and the results of a calibration procedure discussed below. The finalized image data can then be represented as a fully-dimensioned three-dimensional object that can be measured or viewed on the display of computer monitor 56 in any orientation, using conventional software.

With respect to FIG. 2a, a preferred embodiment of second optical subsystem 21 comprises a lamp 21(5) that produces a light beam which illuminates through a heat filter 21(3) and illuminator optics 21(2) onto a grating pattern (not shown) which has been formed, e.g., on a transparent slide that is held in place by slide holder. The illuminated grating pattern is then projected by projection lens onto material surface 7. The requisite phase shifting of the sinusoidal grating pattern is achieved by a method, known as spatial phase shifting, in which the slide holder is not physically moved, and camera 30 takes just one exposure. The data phase shifting is accomplished by means of data processing system 14 processing neighboring pixels that are approximately at 90°, and 180° (and, for four-bucket algorithms, 270°) in phase apart from the original set of pixels corresponding to the first frame at 0°. Other phase-shifting techniques are possible. A test calibration fixture can be used to provide a set of points in three-dimensional space whose coordinates are known very accurately relative to one another. The location of a particular point determined by measuring three adjacent surfaces and then computing their unique intersection point. Each calibration fixture comprises a variety of multi-faceted shapes that are rigidly mounted to a structure to insure their geometrical stability. A test calibration fixture is characterized by a plurality of substantially identical truncated pyramids each having countersunk pins. The calibration procedure for the present invention is described in the cross-referenced patent application.

FIG. 3 shows a block diagram of vision inspection system 4 according to a first embodiment of the present invention, including optical system 6 and data processing system 14 of vision inspection system 4. Data processing system 14, according to one embodiment, includes a video monitor 51, a VME computer system 52, control circuitry 54, robot arm computer 55, and a computer monitor 56 connected to VME computer system 52. Other computer systems can be substituted for VME computer system 52. According to one embodiment of the present invention, VME computer system 52 includes a VME chassis with an embedded Sun Microsystems SPARC 2 single board computer (SBC). Connected to the chassis of VME computer system 52 is a frame grabber 60 such as for example a FG100-VME frame grabber unit manufactured by Imaging Technology, Inc., of Massachusetts, a digital parallel input output unit 61, a multiprocessor 62, and an embedded SPARC 2 processor 63. Multiprocessor 62 may include one or more cards of multiple processors each connected into the VME chassis and including one or more processors which operate as slaves to embedded SPARC 2 SBC, in order to speed image processing operation. Frame grabber 60 receives analog video information from video camera 30 with respect to viewed surface regions 7. The analog signal information is converted into digital form in frame grabber 60 which then provides the received view in digital form to video monitor 51 for operator observation of single frames of information. Control circuitry 54 is connected to frame grabber 60 along an OES signal line, which represents odd even synchronization information regarding whether odd or even video lines are being processed by frame grabber 60. Additionally, an eight-bit COMM/8 line connects control circuitry 54 with parallel input output card 61, enabling the transmission of command control and synchronization information to ensure that information is received by frame grabber 60 at the appropriate illumination times by triggering first and second optical subsystems 20 and 21. Further, control circuitry 54 is connected along a two-way RS232 line with robot arm computer 55. Additionally, monitor 56 is connected to frame grabber 60. As suggested above, optical system 6 includes flash system 19, camera 30, and first and second optical subsystems, 20 and 21, respectively a diffuse flash system and a fringe flash system. Respective first and second optical subsystems 20 and 21 receive trigger signals from flash system 19 which includes a camera flash unit and a flash power supply. Separate trigger signals are provided to first and second optical subsystems 20 and 21, with the diffuse flash receiving a diffuse flash trigger signal and the fringe flash receiving a fringe trigger signal. According to an embodiment of the present invention, first and second optical subsystems 20 and 21 are alternately triggered, so that a particular selected surface region is alternately illuminated and consequently the frames observed by camera 30 represent multiplexed inspection patterns produced under different lighting conditions, in one case adapted to optimize detection and measurement of abrupt surface changes and in the other case adapted to optimize detection and measurement of gradual surface changes.

FIG. 4 is a flow chart of operation of a vision inspection system 4 according to the present invention. According to an embodiment of the present invention, a reference shuttle data base 70 which has previously been constructed is started up 71 to produce object data. Alternatively, operation can begin with a null data base which does not contain any object data. However, if object data has already been collected, according to one embodiment of the present invention, the data base includes measured objects which are characterized according to a predetermined set of object features, such as closed rectangles or ovals, or open figures such as lines or curves, to name several examples. For each feature of an object, predetermined information regarding to parameters specific to the particular feature of an object are included in the data base to specifically identify the qualities of the particular object. The reference shuttle data base 70 stores all radiator measured objects including both artifact and damage information, and this data base is used to initialize the radiator inspection process with known artifact and damage information. The reference shuttle data base 70 includes object data including location data, and feature data, without limitation. The reference shuttle data base 70 further includes an active features list. Reference shuttle data base 70 further includes a features list, as well as, according to one embodiment, the actual radiator image data stored in toto on optical data or video data disk storage. The object data is provided to a data correlator 75 to enable removal of known artifacts and damage from a current data assembly of new objects, permitting retention in the final data base only of new and unknown damage-like objects. Data correlator 75 further correlates object data from both micro and macro data processes, to prevent retention of multiple object representations of the same physical structure. In summary, data correlator 75 accomplishes data correlation in first and second steps, by first accomplishing positional data correlation of macrodata and microdata, and then by accomplishing positional and feature correlation of the results of macro and micro data which amount to eliminate features which amount to no variation from an earlier shuttle database.

Macroframe data which is read by camera 30 is fringe processed 73 and subject to feature measurement 74 and then provided to a data correlator 75 for subsequent data correlation. According to one embodiment of the present invention, the detected image frame information is averaged or shrinked to increase the signal to noise ratio of the information acquired. Next, raw phase information is calculated, based upon a surface profile modulo 1 fringe spacing, according to one embodiment of the present invention. For example, according to one embodiment of the present invention, a four-bucket algorithm is used, wherein the frames are, relatively speaking, at 0° phase, 90° phase, 180° phase, and 270° phase for reasons indicated below. Another alternative method is the Carré method. In the Carré method, the phase shifts between frames can be other than 90°. These are just two examples of algorithms borrowed from phase-shifting interferometry. Any phase-shifting algorithm may be used in the present invention. The raw phase information is then unwrapped to generate a full surface profile amounting to a 3-D profile map of selected patch of material surface 7 based upon macroframe features. In particular, following the calculation of a phase map and the unwrapping of the phases, the computed phases are then converted into calculated three-dimensional coordinates by applying the system calibration parameters to each pixel data point, using the system geometry equations and the results of a calibration procedure detailed in the cross-referenced patent application. The finalized image data can then be represented as a fully-dimensioned three-dimensional object that can be measured or viewed on the display computer monitor 56 in any orientation, using conventional software. A detection filter is applied to the surface profile data. Then, the detected objects are labeled. Similarly, microframe data is read by camera 30 and is detection processed 76.

Next, the microframe data is subject to feature measurement 77. Feature measurement 77 provides measurement data of selected non-damage features to avoid filling the data base with expected features. Measurement of multiple features on an object enable separation of new damage from previously measured artifacts or damage. Accordingly, several features are measured on each detected "damage-like" object, and selection of good feature sets is accomplished by a selected feature performance analysis. Generic aspects of features include length, width, size, rotation angle, shape and the like. Artifact features include bolt-likeness, tape edge-likeness and the like. Next, finalized image data is developed with the use of selected image segmentation techniques. The finalized image data are then used to detect and label potential damage sites.

The data developed according to the system and process of FIG. 4, in respective feature measurement functions 74 and 77 for microdamage and macrodamage frames is then provided to a data correlator 75 for data correlation based upon preestablished object data produced during data base start-up. The purpose of data correlation is to correlate object data from the separate micro and macro damage processes and to correlate object data with known artifacts and damage from a previous data base. Further, a purpose of data correlation is to remove known artifacts and damage from the new object list to pass only new and unknown "damage-like" objects. Both positional and feature correlation is accomplished, to accommodate changes in artifacts and changes in damage. The results of correlation 75 are provided 79 to make a data base update, resulting in a new shuttle data base 80.

The present invention has been particularly described above in terms of certain exemplary embodiments. However, practitioners skilled in the art of optical design, after having perused the foregoing description and the accompanying drawing, could readily develop design forms for other embodiments without departing from the scope of the present invention. Therefore, the present invention is defined more generally by the following claims and their equivalents.

What is claimed is:

1. An optical system for inspecting characteristically different kinds of variations in a surface, said system comprising:

first and second optical subsystems for multiplexed illumination of a predetermined sequence of selected common portions of a material surface region under optical inspection sequenced in alternating succession;

said first optical subsystem providing diffuse illumination;

said second optical subsystem providing fringe illumination taking into account phase information;

an inspection subsystem for viewing common portions of material surface regions in connection with illumination by said first and second optical subsystems; and a data processing system for processing optical inspection data from both said first and second optical subsystems; wherein said second optical subsystem comprises a module for performing ordered phase unwrapping, in which a raw phase map having many pixels is produced, and a quality metric is applied to each pixel in the raw phase map to rank pixels for an order in which they will be unwrapped.

2. The optical system according to claim 1, wherein said data processing system produces a consolidated data base summarizing multiple kinds of surface variations in a selected inspection surface which has been inspected by both said first and second optical subsystems.

3. The optical system according to claim 1, comprising a system for positioning said first and second optical subsystems with respect to common portions of a material surface to be visually inspected.

4. The optical system according to claim 1, comprising a system for carrying said first and second optical subsystems along a predetermined path on a material surface under visual inspection.

5. The optical system according to claim 4, comprising a system for conducting a raster illumination and detection scan of a selected material surface.

6. The optical system according to claim 1, wherein said data processing system compares current data from said first and second optical subsystems with earlier data as to corresponding inspected locations taken by said first and second optical subsystems.

7. The optical system according to claim 1, wherein said first optical subsystem includes a first illumination system for general illumination of a selected portion of a region under optical inspection.

8. The optical system according to claim 1, wherein said second optical subsystem includes a second illumination system for fringe line illumination of a selected portion of a region under optical inspection.

9. The optical system according to claim 1, wherein said first optical subsystem includes a first illumination system for general illumination of a selected portion of a region under optical inspection, and said second optical subsystem includes a second illumination system for fringe line illumination of a selected portion of a region under optical inspection.

10. The optical system according to claim 9, wherein said first illumination system is a diffuse illuminator.

11. The optical system according to claim 9, wherein said first illumination system includes a ring flash lamp.

12. The optical system according to claim 9, wherein said first illumination system includes an elliptical reflector.

13. An optical system for inspecting characteristically different kinds of variations in a surface including both gradual and abrupt surface variations, said system comprising:

first and second optical subsystems for multiplexed illumination and inspection of a predetermined sequence of selected common portions of a material surface region under optical inspection, said first optical subsystem illuminating a coincident area to highlight abrupt surface variations and said second optical subsystem including an illumination system which produces fringe lines taking into account phase information for highlighting gradual surface variations; and a data processing system for processing optical inspection data from both said first and second optical subsystems; wherein second optical subsystem comprises a module for performing ordered phase unwrapping, in which a raw phase map having many pixels is produced, and a quality metric is applied to each pixel in the raw phase map to rank pixels for an order in which they will be unwrapped.

14. The optical system according to claim 13, comprising a video detection system which detects illuminated images highlighted by said first and second optical subsystems during successive illumination intervals.

15. The optical system according to claim 13, wherein said first and second optical subsystems are mounted on a common beam.

16. The optical system according to claim 15, wherein said first and second optical subsystems are laterally offset from each other with respect to common surface areas under alternating illumination.

17. The optical system according to claim 13, wherein said data processing system includes a data correlator for comparing observed surface features with a preestablished data base of surface features.

18. The optical system according to claim 13, said data processing system further comprising a parallel processing system for processing microdamage and macrodamage information to identify both microdamage and macrodamage features.

19. A method of inspecting a surface having macrodamage and microdamage features with a multimode illumination system highlighting microdamage features during one mode of illumination and highlighting macrodamage features in another mode of illumination and including an optical detection system for image detection of illuminated macrodamage and microdamage features, said method including the steps of:

projecting fringe illumination taking into account phase information onto a selected surface patch;

image detecting macrodamage features within the selected surface patch;

projecting diffuse illumination onto the selected surface patch; and image detecting microdamage features within the selected surface patch; wherein said step of projecting fringe illumination is a single-set-of-fringe-lines process for measuring in three-dimensional coordinates the surface shape contours of the surface patch, said process comprising the substeps of:

placing the surface patch into the field of view of a projector assembly;

activating the projector assembly to project a single set of fringe lines on the surface patch to obtain a raw phase map giving a phase at each of a plurality of pixels corresponding to the surface patch;

unwrapping the phases using ordered phase unwrapping; and converting the set of unwrapped phases onto a set of three-dimensional coordinates.

20. The method of claim 19 further comprising processing image detection data for micro- and macrofeatures to measure predetermined surface features.

21. The method of claim 20 including correlation of measured surface features with surface features of a preestablished data base of features.

22. The method of claim 19 wherein the projector assembly comprises:

a fringe line projector that illuminates the surface patch with a single set of fringe lines of sinusoidally varying intensity; and a camera having a field of view that includes at least a portion of said surface patch illuminated by the fringe lines; wherein a single camera frame of data is entered into with a stationary transparent slide that contains said fringe lines, said slide being located within said projector, by means of commanding a computer that is coupled to the camera to sequentially process sets of pixels that are spatially separated from each other on said frame of camera data by specified amounts of phase shift.

* * * * *